United States Patent
Varner et al.

(10) Patent No.: US 9,180,046 B2
(45) Date of Patent: *Nov. 10, 2015

(54) RESERVOIR DEVICE FOR INTRAOCULAR DRUG DELIVERY

(71) Applicant: The Johns Hopkins University School of Medicine, Baltimore, MD (US)

(72) Inventors: Signe Erickson Varner, Menlo Park, CA (US); Eugene De Juan, Menlo Park, CA (US); Aaron Christopher Barnes, Menlo Park, CA (US); Terry Harrison Shelley, Menlo Park, CA (US); Michael J. Cooney, Menlo Park, CA (US)

(73) Assignee: THE JOHNS HOPKINS UNIVERSITY SCHOOL OF MEDICINE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/942,610

(22) Filed: Jul. 15, 2013

(65) Prior Publication Data

US 2013/0304031 A1 Nov. 14, 2013

Related U.S. Application Data

(60) Continuation of application No. 12/979,185, filed on Dec. 27, 2010, now Pat. No. 8,486,052, which is a division of application No. 10/171,406, filed on Jun. 12, 2002, now Pat. No. 7,883,717.

(60) Provisional application No. 60/297,499, filed on Jun. 12, 2001.

(51) Int. Cl.
*A61K 9/00* (2006.01)
*A61F 9/00* (2006.01)
*A61M 5/00* (2006.01)

(52) U.S. Cl.
CPC ....... *A61F 9/0017* (2013.01); *A61F 2250/0067* (2013.01)

(58) Field of Classification Search
None
See application file for complete search history.

(56) References Cited

U.S. PATENT DOCUMENTS

| | | | |
|---|---|---|---|
| 2,564,977 A | 8/1951 | Hu et al. | |
| 2,585,815 A | 2/1952 | McLintock | |
| 3,232,117 A | 2/1966 | Gilmont | |
| 3,416,530 A | 12/1968 | Ness | |
| 3,618,604 A | 11/1971 | Ness | |
| 3,641,237 A | 2/1972 | Gould et al. | |
| 3,828,777 A | 8/1974 | Ness | |
| 3,831,583 A | 8/1974 | Edmunds, Jr. et al. | |
| 3,845,201 A | 10/1974 | Haddad et al. | |
| 3,902,495 A | 9/1975 | Weiss et al. | |
| 3,914,402 A | 10/1975 | Shell | |
| 3,916,899 A | 11/1975 | Theeuwes et al. | |
| 3,926,188 A | 12/1975 | Baker et al. | |
| 3,949,748 A | 4/1976 | Malmin | |
| 3,949,750 A | 4/1976 | Freeman | |
| 3,961,628 A | 6/1976 | Arnold | |
| 3,977,404 A * | 8/1976 | Theeuwes | 424/427 |
| 3,995,635 A | 12/1976 | Higuchi et al. | |
| 4,008,719 A | 2/1977 | Theeuwes et al. | |
| 4,014,333 A | 3/1977 | McIntyre | |
| 4,014,334 A | 3/1977 | Theeuwes et al. | |
| 4,014,335 A | 3/1977 | Arnold | |
| 4,034,756 A | 7/1977 | Higuchi et al. | |
| 4,034,758 A | 7/1977 | Theeuwes | |
| 4,077,407 A | 3/1978 | Theeuwes et al. | |
| 4,111,201 A | 9/1978 | Theeuwes | |
| 4,111,203 A | 9/1978 | Theeuwes | |
| 4,135,514 A | 1/1979 | Zaffaroni et al. | |
| 4,160,452 A | 7/1979 | Theeuwes | |
| 4,164,559 A | 8/1979 | Miyata et al. | |
| 4,179,497 A | 12/1979 | Cohen et al. | |
| 4,186,184 A | 1/1980 | Zaffaroni | |
| 4,200,098 A | 4/1980 | Ayer et al. | |
| 4,220,152 A | 9/1980 | Dresback | |
| 4,220,153 A | 9/1980 | Dresback | |
| 4,256,108 A | 3/1981 | Theeuwes | |
| 4,298,000 A | 11/1981 | Thill et al. | |
| 4,300,557 A * | 11/1981 | Refojo et al. | 424/424 |
| 4,309,776 A | 1/1982 | Berguer | |
| 4,326,525 A | 4/1982 | Swanson et al. | |
| 4,327,725 A | 5/1982 | Cortese et al. | |
| 4,343,787 A | 8/1982 | Katz | |
| 4,439,196 A | 3/1984 | Higuchi | |
| 4,439,198 A | 3/1984 | Brightman, II et al. | |
| 4,475,916 A | 10/1984 | Himmelstein | |
| 4,484,922 A | 11/1984 | Rosenwald | |
| 4,519,801 A | 5/1985 | Edgren | |

(Continued)

FOREIGN PATENT DOCUMENTS

| | | |
|---|---|---|
| EP | 0033042 B1 | 8/1981 |
| EP | 0228185 A1 | 11/1986 |

(Continued)

OTHER PUBLICATIONS

Andrews, "Effect of nonsteroidal anti-inflammatory drugs on LFA-1 and ICAM-1 expression in gastric mucosa," Am J Physiol. Apr. 1994;266(4 Pt 1):G657-664.

(Continued)

*Primary Examiner* — Robert A Wax
*Assistant Examiner* — Randeep Singh
(74) *Attorney, Agent, or Firm* — Fred C. Hernandez; Mintz Levin Cohn Ferris Glovsky and Popeo, P.C.

(57) ABSTRACT

A delivery device that allows for the sustained release of an agent, particularly useful for the sustained release of a therapeutic agent to limited access regions, such as the posterior chamber of the eye and inner ear. The delivery device is minimally invasive, refillable and may be easily fixed to the treatment area. The delivery device includes a hollow body with an inlet port at its proximal end for insertion of the agent, a reservoir for holding the agent and a delivery mechanism for the sustained delivery of the agent from the reservoir to the patient.

21 Claims, 5 Drawing Sheets

(56) References Cited

U.S. PATENT DOCUMENTS

| | | |
|---|---|---|
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,516,522 A | 5/1996 | Peyman et al. |
| 5,554,132 A | 9/1996 | Straits et al. |
| 5,562,915 A | 10/1996 | Lowe et al. |
| 5,576,480 A | 11/1996 | Hopkins et al. |
| 5,578,042 A | 11/1996 | Cumming |
| 5,681,572 A | 10/1997 | Seare, Jr. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A * | 10/1998 | Wong ............... 128/898 |
| 5,830,173 A | 11/1998 | Avery et al. |
| 5,830,492 A | 11/1998 | Usala |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,096,070 A | 8/2000 | Ragheb et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,094,226 B2 | 8/2006 | Yaacobi |
| 7,141,023 B2 | 11/2006 | Diermann et al. |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,476,510 B2 | 1/2009 | Kapur et al. |
| 7,621,907 B2 | 11/2009 | Rodstrom |
| 7,883,717 B2 | 2/2011 | Varner et al. |
| 7,914,442 B1 | 3/2011 | Gazdzinski |
| 7,973,068 B2 | 7/2011 | Demopulos et al. |
| 8,486,052 B2 | 7/2013 | Varner et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2004/0011651 A1 | 1/2004 | Becker et al. |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2005/0112175 A1 | 5/2005 | Yaacobi |
| 2005/0113806 A1 | 5/2005 | De Carvalho et al. |
| 2005/0119737 A1 | 6/2005 | Bene et al. |
| 2006/0246112 A1 | 11/2006 | Snyder et al. |
| 2008/0161741 A1 | 7/2008 | Bene et al. |
| 2009/0061071 A1 | 3/2009 | McMorrow et al. |
| 2010/0022945 A1 | 1/2010 | Rodstrom |
| 2010/0100043 A1 | 4/2010 | Racenet |
| 2010/0221309 A1 | 9/2010 | Myers et al. |
| 2011/0208122 A1 | 8/2011 | Shekalim |
| 2012/0184905 A1 | 7/2012 | Shekalim |

FOREIGN PATENT DOCUMENTS

| | | |
|---|---|---|
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1385452 | 9/2006 |
| EP | 1409065 | 1/2007 |
| EP | 1337284 B1 | 12/2007 |
| JP | 01-149716 | 6/1989 |
| JP | 01-197429 A | 8/1989 |
| WO | WO-8804573 A1 | 6/1988 |

(56) References Cited

FOREIGN PATENT DOCUMENTS

| WO | WO-9007545 A2 | 7/1990 |
| --- | --- | --- |
| WO | WO-9528984 | 11/1995 |
| WO | WO-9729850 | 8/1997 |
| WO | WO-9825982 | 6/1998 |
| WO | WO-9843611 A1 | 10/1998 |
| WO | WO-9911244 | 3/1999 |
| WO | WO-0048660 | 8/2000 |
| WO | WO-0126714 | 4/2001 |
| WO | WO-0150943 | 7/2001 |
| WO | WO-0168016 | 9/2001 |
| WO | WO-02053128 A2 | 7/2002 |
| WO | WO-02100318 | 12/2002 |
| WO | WO-03028765 | 4/2003 |
| WO | WO-03077972 | 9/2003 |
| WO | WO-03082188 | 10/2003 |
| WO | WO-2007035473 | 3/2007 |

OTHER PUBLICATIONS

Bird et al., Transport Phenomena, John Wiley & Sons, Inc., New York, 1960, pp. 196-201.
Block et al., "Solubility and dissolution of triamcinolone acetonide," Journal of Pharmaceutical Sciences, Apr. 1973; 62(4):617-621.
Breslin, C.W., et al., "Chapter 7. Slow Release Artificial Tears", *Symposium on Ocular Therapy* pp. 77-83, 1977.
Chirila et al., "*The* Vitreous Humor" in *Handbook of Biomaterial Properties*, eds. Black & Hastings. Chapman & Hall, London, 1998; pp. 125-131.
European Search Report: Form EPO1503 for Application No. 10184729.1-2319, dated Mar. 4, 2011, 1 page.
Hastedt & Wright, "Diffusion in porous materials above the percolation threshold," Pharm. Res. Sep. 1990; 7(9):893-901 (1990).
Heier et al, "Ketorolac versus prednisolone versus combination therapy in the treatment of acute pseudophakic cystoid macular edema," Ophthalmology. Nov. 2000;107(11):2034-2038 ;discussion 2039.
International Search Report: Form PCT/ISA210, for Application No. PCT/US2002/18642, dated May 23, 2003, 3 pages.
Kang et al., "Inhibitory effects of anti-inflammatory drugs on interleukin-6 bioactivity," Biol Pharm Bull. Jun. 2001;24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", *Ophthalmology* 85 (1978) pp. 794-800.
Lee, D.A., et al., "Glaucoma Filtration Surgery in Rabbits Using Bioerodible Polymers and 5-Fluorouracil", *Ophthalmology* 94:12 (1987) pp. 1523-1530.
Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.
Miller, DP, et al., *Thermophysical Properties of Trehalose and Its Concentrated Aqueous Solutions*, Pharmaceutical Research, vol. 14, No. 5, 1997, pp. 578-590.
Moritera, T., et al., "Microspheres of Biodegradable Polymers as a Drug-Delivery System in the Vitreous", *Investigative Ophthalmology & Visual Science* 32-6 (1991) pp. 1785-1790.
Saline (medicine)—Wikipedia, the free encyclopedia. http://web.archive.org/web/20110205192937/http://en.wikipedia.org/wiki/Saline_(medicine). Apr. 27, 2012.
Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthalmol* 110 (1992) pp. 255-258.
Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.
Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.
Carbonaro, et al. "Nano-pore silicon membrane characterization by diffusion and electrical resistance." *Journal of Membrane Science*. 241 (2004):249-255.
Jornitz et al. "Filter Integrity Testing in Liquid Applications, Revisited; Part 1." *Pharmaceutical Technology*. Oct. 2001. pp. 34-50.
Millipore. "Filter Integrity Test Methods." *Millipore Corporation*. 1999.

\* cited by examiner

RESERVOIR DEVICE FOR INTRAOCULAR DRUG DELIVERY

CROSS-REFERENCES TO RELATED APPLICATIONS

The present application is a Continuation of co-pending U.S. patent application Ser. No. 12/979,185, filed Dec. 27, 2010, which is a Divisional of U.S. patent application Ser. No. 10/171,406, filed Jun. 12, 2002, now U.S. Pat. No. 7,883,717, which claims the benefit of U.S. provisional application Ser. No. 60/297,499, filed Jun. 12, 2001. The priority of the filing dates is hereby claimed, and the disclosures of each of the above-mentioned patent applications are hereby incorporated by reference in their entirety.

BACKGROUND

The present invention relates to improved delivery devices and methods of use. More particularly, the present invention relates to minimally invasive, refillable, sustained release delivery devices particularly suitable for the delivery of therapeutic agents to limited access regions, such as the posterior chamber of the eye.

The delivery of drugs to the eye presents many challenges. The ocular absorption of systemically administered pharmacologic agents is limited by the blood ocular barrier, namely the tight junctions of the retinal pigment epithelium and vascular endothelial cells. High systemic doses can penetrate this blood ocular barrier in relatively small amounts, but expose the patient to the risk of systemic toxicity. Topical delivery of drugs often results in limited ocular absorption due to the complex hydrophobic/hydrophilic properties of the cornea and sclera. Additionally, topical agents are mechanically removed by the blink mechanism such that only approximately 15% of a single drop is absorbed. Diffusion of topically administered drugs to the posterior chamber occurs, but often at sub-therapeutic levels. Intravitreal injection of drugs is an effective means of delivering a drug to the posterior segment in high concentrations. However, these repeated intraocular injections carry the risk of infection, hemorrhage and retinal detachment. Patients also find this procedure somewhat difficult to endure.

Local sustained delivery of therapeutics to the posterior chamber is critical in managing several chronic diseases of the eye. To address this need, several drug delivery devices have been developed for intraocular insertion into the vitreous region of the eye.

U.S. Pat. No. 4,300,557, for example, describes an intraocular implant in the form of a silicone capsule which can be filled with a drug to be delivered. The capsule is inserted in the vitreous region of the eye by making an incision in the eye, inserting the capsule and closing the incision. The capsule remains in place for a period of time and may be removed by making a second surgical incision into the eye and retrieving the device. The capsule has an attached tube which passes through the surface of the eye and extends outward from the eye useful for the subsequent injection of a drug. While in the vitreous, the device is not anchored and may move about freely.

U.S. Pat. No. 5,378,475 (often referred to as Vitrasert) describes a device 15 which has been developed for insertion in the vitreous region of the eye, and is described in T. J. Smith et al., Sustained-Release Ganciclovir, Arch. Ophthalmol, 110, 255-258 (1992) and G. E. Sanborn, et al., Sustained-Release Ganciclovir Therapy for Treatment of Cytomegalovirus Retinitis. Use of an Intravitreal Device, Arch. Ophthalmol, 110, 188-195 (1992). This device consists of an inner core of pharmacologic agent surrounded by two coatings with different permeabilities. Drug diffuses through a small opening in one of these coatings achieving near-order release kinetics. It is implanted in the region of the pars plana through a 3.5-5.0 mm scleral incision. The implant must be removed and replaced every 6 months in the operating room as the drug becomes depleted. There is an approximately 25% complication rate from these procedures. The device is membrane diffusion drug delivery system that relies on EVA/PVA polymers to mediate release rate. Thus, many agents cannot be effectively delivered from such a system because their permeation rate through the rate controlling material of the system is too small to produce a useful effect. Other agents cannot be satisfactorily delivered by diffusional devices because of a particular chemical characteristic of the agent. This includes salts, because of their ionic character, and unstable polar compounds that cannot be formulated into a composition suitable for storage and delivery from such systems.

U.S. Pat. No. 5,098,443 describes a series of C-shaped rings that are inserted through incisions made in the eye wall or sutured around the globe of the eye. These rings may be formed from biodegradable polymers containing microparticles of drug. Alternatively, the implant may be in the form of a hollow flexible polymeric cocoon with the drug disposed therewithin for slow release by osmosis. No anchoring device is described.

U.S. Pat. No. 5,466,233 describes a tack for intraocular drug delivery. This device has an end that is positioned in the vitreous cavity while the head remains external to the eye and abuts the scleral surface. The drug is contained in the vitreous end of the device and could be contained within a biodegradable or nonbiodegradable scaffold. Alternatively, the device may have a hollow core filled with a drug that could diffuse through the wall of the tack into the eye. This core could be refillable. The head of the tack may further have a suture hole for anchoring the sclera.

While intraocular devices exist which allow delivery of therapeutic agents to the eye, a need still remains for a device which accomplishes controlled, sustained delivery to the posterior chamber, is implantable and removable without requiring long full thickness scleral incisions, does not cause undue patient irritation or discomfort, is stable within the vitreous region of the eye, is refillable and dose titratable, and is capable of delivering a wide range of small molecule, gene and protein therapeutics.

SUMMARY

The present invention provides a delivery device and methods of use. More particularly, the present invention relates to a sustained release delivery device that is minimally invasive and refillable. The delivery device of the present invention is particularly suitable for the delivery of therapeutic agents to the posterior chamber of the eye and other limited access regions.

An exemplary embodiment of the delivery device includes a reservoir having an inlet port at its proximal end for insertion of the agent. A scleral hub, or similar fixation element, may further be located near the proximal end for suturing or otherwise securing the device at a desired location. The agent inserted into the reservoir through the inlet port is delivered to a treatment area by a delivery mechanism located along the reservoir and/or at the distal end of the reservoir. For example, in one embodiment, the agent may be delivered through the reservoir by, for example, forming the reservoir of a material that is permeable to the agent or, for example, providing one or more apertures in the reservoir through which the agent may flow. In another embodiment, the delivery mechanism is located at the distal end of the reservoir by, for example, forming the distal end of the reservoir of a semi-permeable membrane or providing one or more apertures in the distal end of the reservoir. The reservoir is preferably fabricated of a pliable material that allows the reservoir to be compressed for insertion through a small incision. Once inside the incision, the reservoir may automatically unfold and/or as agent is injected through the inlet port, the reservoir may unfold as it is filled with the agent.

The drug delivery device may further include a hollow body or tube inside the reservoir, wherein the proximal end of the hollow body or tube forms the inlet port. In this embodiment, hollow body or tube may provide structural rigidity that facilitates insertion of the device through a small incision. The reservoir covers at least a portion of the length of the hollow body or tube and is preferably pliable so that it may be folded, rolled and/or compressed about the hollow body or tube to enable insertion of the device through a small incision not much larger than the size of the hollow body or tube. At least one aperture in the hollow body or tube provides communication between the contents of the hollow body or tube and the reservoir such that, as the agent is inserted through the inlet port, it travels through the hollow body or tube, through the aperture(s) and into the reservoir. As the agent fills the reservoir, the reservoir unfolds. In one embodiment, the distal end of the hollow body or tube extends outside the reservoir and forms a delivery port through which the agent is delivered to the patient. In another embodiment, the therapeutic agent is delivered to the patient through the reservoir by, for example, forming the reservoir of a material that is permeable to the agent or, for example, providing one or more apertures in the reservoir through which agent may flow. A scleral hub, or similar fixation element, may further be located near the proximal end of the hollow body or tube for suturing or otherwise securing the device at a desired location.

Methods for the delivery of an agent are also disclosed. In particular, the methods involve delivery of agents to the eye to treat a variety of ocular conditions such as, for example, retinal detachment, vascular occlusions, proliferative retinopathy, diabetic retinopathy, inflammations such as uveitis, choroiditis and retinitis, degenerative disease, vascular diseases and various tumors including neoplasms.

The methods comprise making a small incision in the eye to provide access to the treatment site. The delivery device is provided in an "empty" state, with the reservoir empty and preferably compressed tightly as shown in FIG. 1a. Compressing the reservoir is desirable since it allows the delivery device to be passed through a small incision that requires few or no sutures for closure. The delivery device is then inserted through the incision distal end first until the scleral hub or fixation mechanism abuts the incision. The scleral hub or fixation mechanism may then be sutured or secured to the sclera to assist in maintaining the device at the treatment site. Once inside the incision, the reservoir may automatically unfold. The therapeutic agent is then injected into the device through the inlet port by use of a syringe or similar mechanism containing with the agent. The agent travels into the reservoir, thereby further unfolding the reservoir. Once reservoir is filled to a desired level, the syringe may be disconnected from the inlet port and the inlet port closed. The agent is then delivered to the patient either through a delivery port or through the reservoir. After delivery of the contents of the reservoir to the patient, the device may be refilled for further delivery of agent or removed. At the time of removal, the reservoir is preferably empty and compressed, thereby allowing the device to be removed through a small incision that requires few or no sutures for closure.

Depending on the particular application, the device may be designed to deliver a desired dose of agent at a particular rate, for example, by providing various sized reservoirs, reservoirs with various permeabilities to the agent, delivery apertures or ports with smaller or larger diameters and delivery ports with rate controlling covers.

The present delivery device and methods of use are minimally invasive. In particular, the delivery device has a small profile that allows it to be inserted through a small opening. Such an insertion procedure eliminates the risks associated with more invasive surgery, and, further, enables such procedures to take place in an office setting. Also, the device can be removed from a small insertion site, requiring few or no sutures for scleral closure. This is a dramatic improvement over state of the art technologies which require surgery for both implantation and removal.

Further, while many existing devices for ocular delivery incorporate the therapeutic agent into the structure of the implant for release via diffusion or bioerosion of the carrier, the delivery device of the present invention is a refillable device easily filled and refilled by injection. This feature allows the physician to easily titrate dosage to the need of the individual patient. Additionally, a single device may be used with a wide range of agents, because the present device avoids implantation of the agent into the structure of the device during the manufacturing process.

Still further, because release of the agent using the present delivery device is not necessarily membrane diffusion regulated, the present device lends itself to the delivery of agents that do not readily permeate through polymeric membranes, such as ionic drugs or proteins.

Other aspects and embodiments of the invention are discussed infra.

DETAILED DESCRIPTION

Figure 1A:
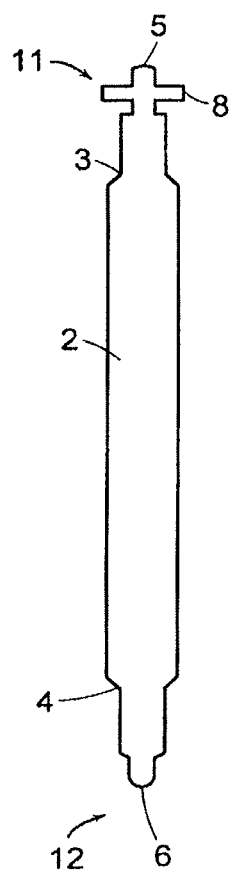
FIG. 1A illustrates an empty delivery device in accordance with an embodiment of the present invention.

Referring now to the various figures of the drawing, wherein like reference characters refer to like parts, there is shown various views of a delivery device 1, in accordance with the invention.

Figure 1B:
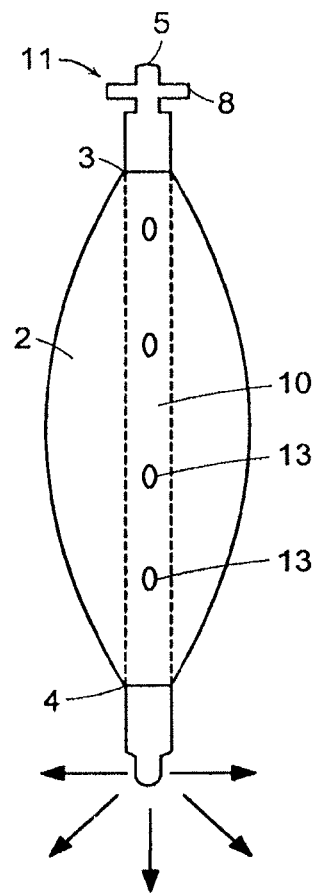
FIG. 1B illustrates the delivery device of FIG. 1a holding an agent.
Figure 2:
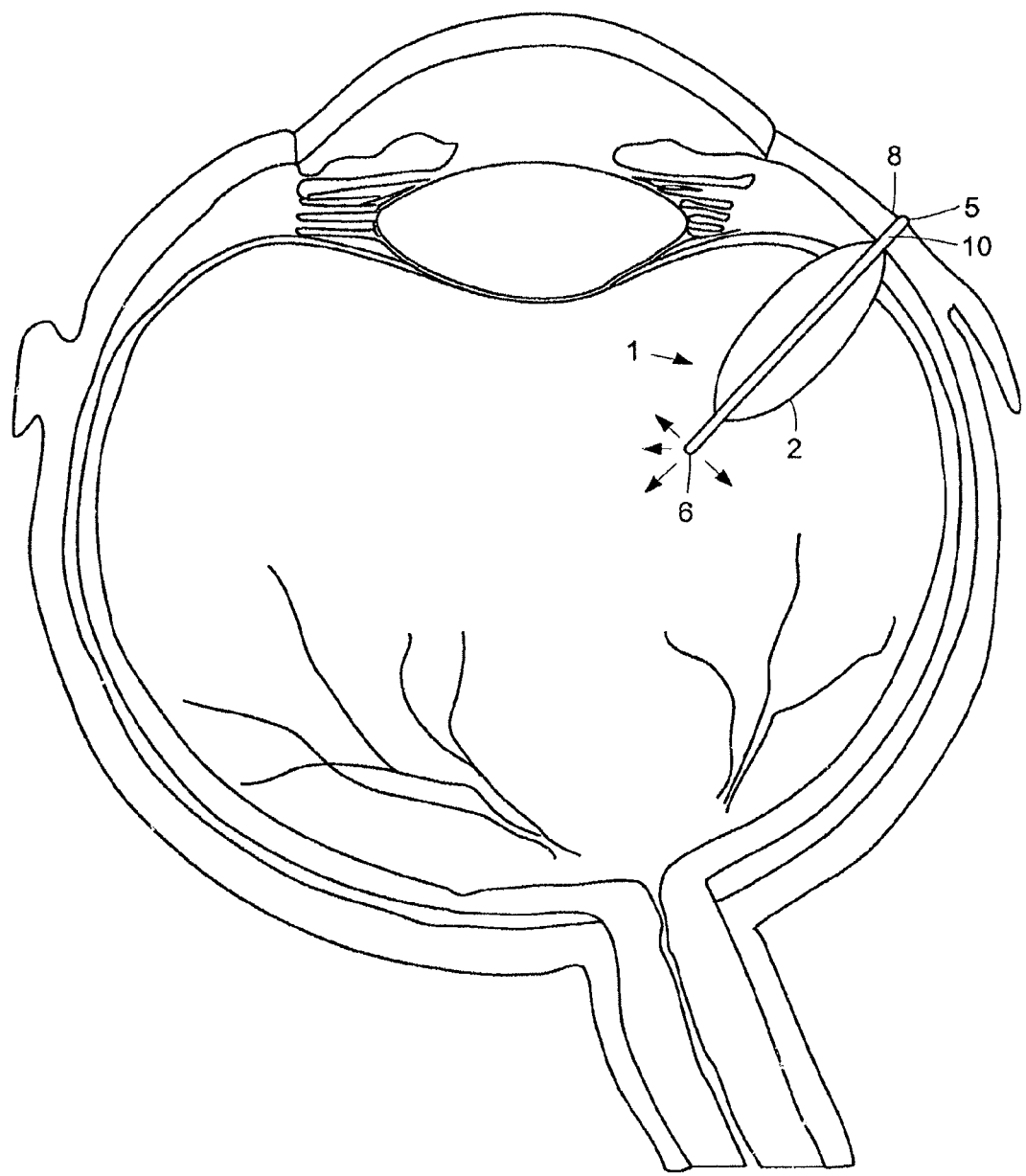
FIG. 2 depicts the final location of the device of FIG. 1a and 1b within the eye.
Figure 3:
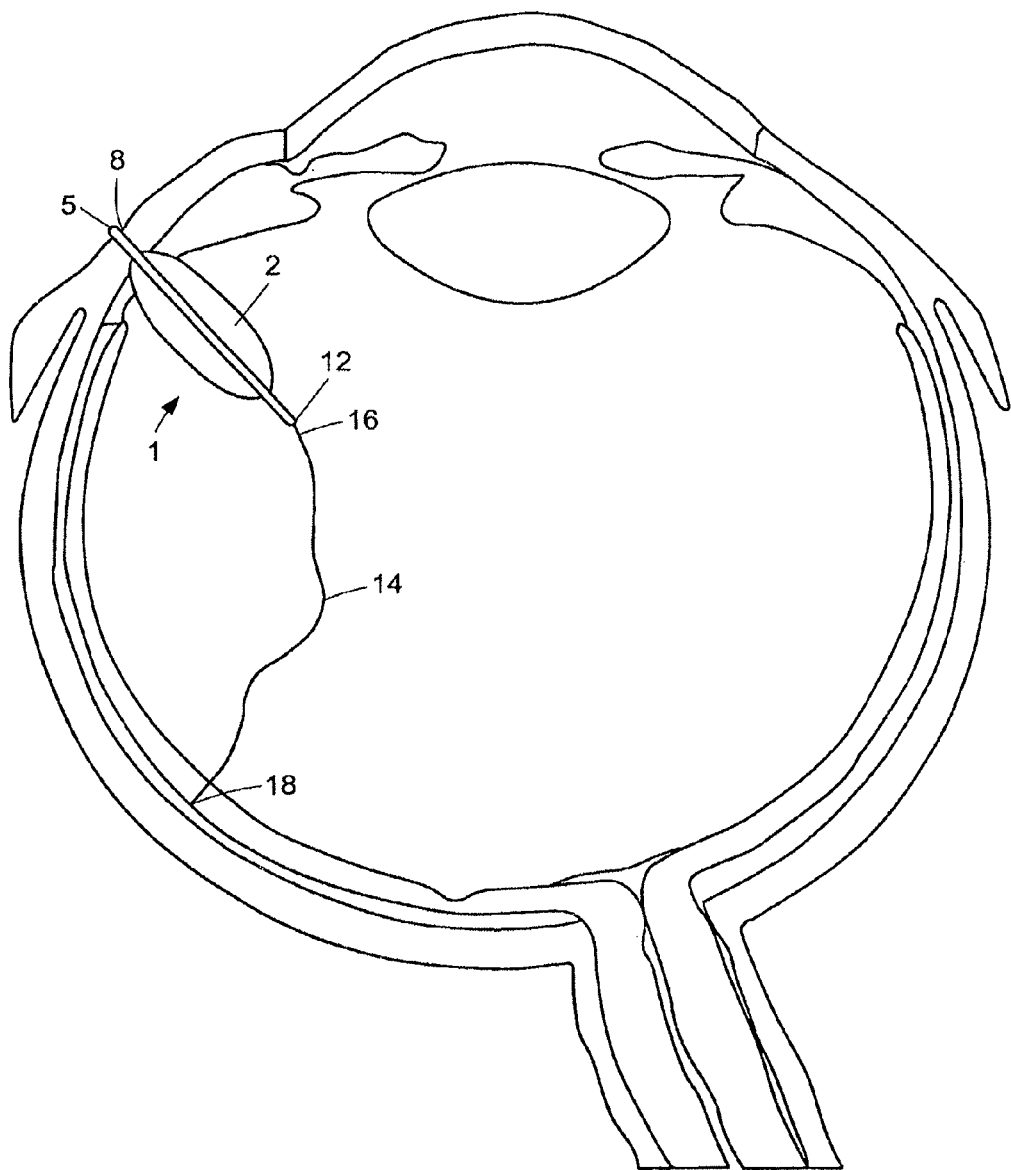
FIG. 3 depicts the final location of the device within the eye in accordance with another embodiment of the present invention.

As shown in FIGS. 1-3, the delivery device 1 includes a reservoir 2 having a proximal end 3 and a distal end 4. Located near the proximal end 3 of the reservoir 2 is an inlet port 5 for injection of a desired agent into the reservoir 1. Agent injected through the inlet port 5 is delivered to the treatment area through delivery mechanism 6.

The delivery device 1 may further include a hollow body or tube 10 housed at least partially within the reservoir 2. The hollow body or tube 10 has a proximal end 11 and a distal end 12. Preferably, the proximal end 11 of the hollow body or tube 10 extends outside the reservoir 2, as shown in FIGS. 1-3, and serves as the inlet port 5 through which the agent is injected into the device.

The materials used in fabricating the reservoir 2 are not particularly limited, provided these materials are biocompatible and preferably insoluble in the body fluids and tissues that the device comes into contact with. In some embodiments, it is further preferred that the materials used in fabricating the reservoir 2 are pliable materials that allows the reservoir 2 to be folded, rolled and/or compressed for insertion through a small incision that requires few or no sutures for closure. Once inside the incision, the reservoir 2 may automatically unfold or unroll to some extent. Additionally, as agent is injected through the inlet port 5 into the reservoir 2, the reservoir 2 may unfold or unroll and expand as it is filled with the agent.

In one preferred embodiment, the reservoir 2 is in the form of a balloon and is fabricated of an elastic material. As the agent is injected into the inlet port 5, the agent passes into the expandable reservoir 2 or balloon, thereby inflating and expanding the reservoir 2 or balloon. Pressure of the elastic material against the agent within the reservoir 2 provides a driving force for delivery of agent through the delivery mechanism 6. Suitable materials for use in forming an elastic reservoir are well known and may be readily determined by one of skill in the art. For example, some suitable include thin-walled nondistensible materials, such as PET, and more elastomeric materials, such as polyurethane. When the reservoir 2 is fabricated of a material such as PET, flow through the delivery mechanism 6 is primarily driven by diffusion and/or intraocular pressure force. When the reservoir 2 is fabricated of a material such as polyurethane, delivery of the agent may be driven, a least in part, by the spring-like properties of the material forming the reservoir 2.

In one embodiment, the delivery mechanism comprises at least a portion of the reservoir 2. For example, this may be accomplished by fabricating at least a portion of the reservoir 2 of a material that is permeable to the agent. Such materials may vary depending on the particular application and the agent to be delivered and may be readily determined by one of skill in the art. For example, this may be accomplished by fabricating at least a portion of the reservoir 2 of a material that is permeable to the agent. Such materials may vary depending on the particular application and the agent to be delivered and may be readily determined by one of skill in the art. By way of example, some suitable permeable materials may include polycarbonates, polyolefins, polyurethanes, copolymers of acrylonitrile, copolymers of polyvinyl chloride, polyamides, polysuiphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers.

The particular material may be chosen to provide a particular rate of delivery of the agent, which may be readily determined by one of skill in the art. The rate of delivery of an agent may also be increased or decreased by varying the percentage of the reservoir 2 formed of the material permeable to the agent. Preferably, to provide a slower rate of delivery, the reservoir 2 may be fabricated of 50% or less permeable material. For example, the reservoir 2 may be fabricated of 1%, 5%, 10%, 20%, 30%, 40% or 50% of permeable material. For a faster rate of delivery, the reservoir may be fabricated of greater than 50% of permeable material. For example, the reservoir 2 may be fabricated of 51%, 55%, 60%, 70%, 80%, 90% or 100% of permeable material.

Figure 4A:
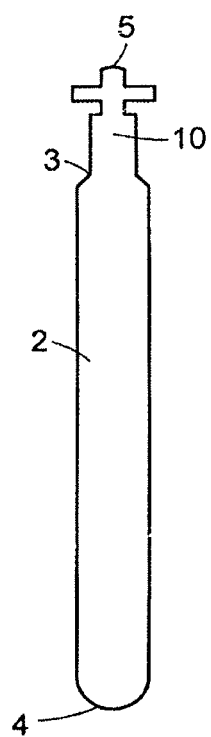
FIG. 4A illustrates an empty delivery device in accordance with another embodiment of the present invention.
Figure 4B:
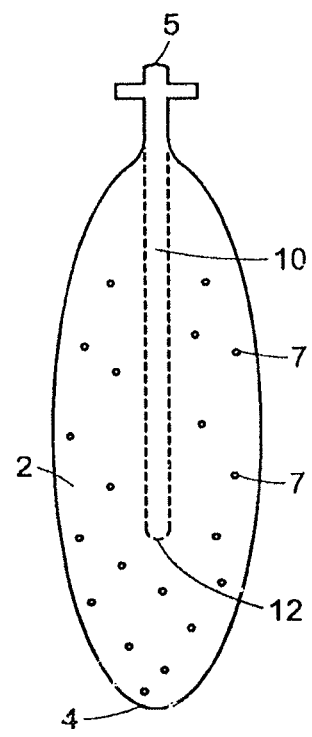
FIG. 4B illustrates the drug delivery device of FIG. 4a holding an agent.

In another embodiment, for example, as shown in FIG. 4b, the delivery mechanism 6 comprises one or more apertures 7 in the reservoir 2 formed, for example, with a laser, hot wire, drilling device or similar mechanism. The one or more apertures 7 may be located along the length of the reservoir 2 and/or at the distal end 4 of the reservoir 2. The number and size of the one or more apertures 7 may vary depending on the desired rate of delivery of the agent and may be readily determined by one of skill in the art.

When the delivery device 1 includes a hollow body or tube 10, the distal end 12 of the hollow body or tube 10 may extend outside the reservoir 2, as shown in FIGS. 1-3, and may serve as the delivery mechanism 6 through which the agent is delivered to the treatment site. In this embodiment, one or more apertures 13 are located through the wall of the hollow body or tube 10 to provide communication between the contents of the hollow body or tube 10 and the reservoir 2. Thus, as the agent is injected through the proximal end 11 of the hollow body or tube 10, which forms the inlet port 5, the agent flows through the hollow body or tube 10 and into the reservoir 2 through the one or more apertures 13 in the wall of the hollow body or tube 10. Preferably, the device 1 is designed such that as the agent is injected into the delivery device 1, all or a majority of the agent injected through the inlet port 5 passes through the hollow body or tube 10 into the reservoir 2 rather than passing directly out of the device through the distal end of the hollow body or tube 10. This may be accomplished by, for example, providing one or more apertures 13 in wall of the hollow body or tube 10 that are larger than or that accommodate greater flow of agent than the delivery mechanism 6. Alternatively, a valve (not shown) or similar mechanism may be located at the delivery mechanism 6 for closing off the delivery mechanism 6 during injection of the agent.

In a preferred embodiment, the distal end 12 of the hollow body or tube 10 is designed to provide controlled delivery of agent from the device. This may be achieved by, for example, providing a distal end 12 with small holes and/or, for example, placing a covering or lining (not shown) over the distal end 12, wherein the covering or lining has a particular porosity to the agent or wherein the covering or lining is fabricated of a diffusion or rate-limiting membrane, matrix material or similar material.

In another embodiment, wherein the distal end 12 of the hollow body or tube 10 extends outside the reservoir 2, it is also possible to design the device such that both the distal end 12 and the reservoir 2 form the delivery mechanism 6. Thus, for example, the distal end 12 may be designed as set out above to deliver the agent and, for example, the reservoir 2 may be fabricated of a permeable material or one or more apertures 7 may be formed in the reservoir 2. Still further, it is possible to have the distal end 12 of the hollow body or tube 10 extend outside the reservoir 2, wherein the distal end 12 is closed off and does not serve as a delivery mechanism but, rather, the reservoir 2 serves as the delivery mechanism 6 by, for example, fabricating the reservoir 2 of a permeable material or forming one or more apertures 7 in the reservoir 2.

In another embodiment wherein the delivery device 1 includes a hollow body or tube 10, the distal end 12 of the hollow body or tube 10 may be contained within the reservoir 2, as shown in FIGS. 4a and 4b. In this embodiment, the delivery mechanism 6 may comprises at least a portion of the reservoir 2 by, for example, forming at least a portion of the reservoir 2 or the entire reservoir 2 of a material that is permeable to the agent, or one or more apertures 7 may be fabricated in the reservoir 2 as described above. In this embodiment, the distal end 12 may have an opening through which the agent travels from the inlet port 5 into the reservoir 2. At least one aperture 13 may alternatively or may also be located along the hollow body or tube 10 through which agent may travel from the inlet port 5 into the reservoir 2.

The hollow body or tube 10 is preferably rigid and provides structural support beneath the reservoir 2 for easier implantation of the device 1 through the incision. As such, the hollow body or tube 10 may be formed of rigid materials including, for example, stainless steel, titanium, nitinol, polymers and other similar materials. As shown in FIGS. 1-4b, the hollow body or tube 10 is preferably cylindrical in shape, with a circular cross-section. However, the shape of the hollow body or tube 10 is not limited and, for example, the hollow body or tube 10 may alternatively have, for example, square, rectangular, octagonal or other cross-sectional shapes.

The reservoir 2 is bonded to the hollow body or tube 10 forming a fluid-tight seal that does not separate from the hollow body or tube 10 during use, thereby preventing leakage of agent out of the device between the hollow body or tube 10 and reservoir 2. Thus may be accomplished by using a variety of adhesives and epoxies.

The inlet port 5 of the delivery device 1 is designed such that the needle of a syringe, or similar injection mechanism, may be inserted through the inlet port 5 and the agent housed within the syringe or injection mechanism may be injected through the inlet port 5 and into the reservoir 2. The inlet port 5 preferably forms a snug seal about the needle of the syringe or injection mechanism to prevent leakage of the agent out of the inlet port around the syringe needle or injection mechanism and to provide sterile injection of agent into the delivery device 1. If desired, fittings or collars (not shown), through which a syringe needle or injection mechanism may be inserted and which form a snug seal about the syringe needle or injection mechanism, may be mounted on the inlet port 5.

Upon injection of the agent into the drug delivery device 1, the needle of the syringe or the injection mechanism is removed from the inlet port 5 and the inlet port 5 sealed. This may be accomplished by providing a removable cover (not shown) on the inlet port 5 that may be removed for injection of the agent and replaced when the agent has been injected. In a preferred embodiment, the inlet port 5 is composed of an injectable self-sealing material through which the needle or injection mechanism may be inserted and which seals off automatically when the needle or injection mechanism is removed. Such materials are known and include, for example, silicone rubber, silicone elastomers and polyolefin.

As shown in FIGS. 1-4b, a fixation mechanism 8, such as, for example, a scleral hub, may further be located near the inlet port 5 to assist in stabilizing the device 1 near the delivery site. Preferably, the delivery device 1 is inserted into the incision until the fixation mechanism 8 abuts the incision. In one embodiment, as shown in FIGS. 1-4b, the fixation mechanism 8 is in the form of extensions from the proximal end 11 of the hollow body or tube 10. These extensions rest on the surface surrounding the incision, as shown in FIGS. 2-3. These extensions may be of any shape, for example, circular, rectangular, triangular, etc. and are sized to provide a surface on which the device I stably rests and to provide a portion that may be sutured or otherwise secured to the surface surrounding the incision. While the extensions are shown as extending approximately perpendicularly from the hollow body of tube 10, the extensions are not limited to such an arrangement and may, for example, be curved away from the device so as to conform to the curvature in the surface of the eye. The overall shape and size of the fixation mechanism 8 is not limited as long as irritation and damage to the surface of the eye or other area of the body that it is in contact with are minimized.

As shown in FIG. 3, the delivery device 1 may further include a tube 14 having a first end 16 and a second end 18, for the delivery of therapeutic agent directly to a target site. For example, the first end 16 of the tube 14 may be connected to the distal end 4 of the reservoir 2 or the distal end .12 of the hollow body or tube 10 and the second end 18 of the tube may be secured to or located proximal to the target site (e.g. the choroids and retinal pigment epithelial cells). The tube 14 may be sized as so as to limit delivery rate, to minimize trauma to the retina, and to minimize leaking of the agent. The tube 14 is preferably fabricated of a flexible material so that small movements of the delivery device 1 will not be translated to the retina, thereby minimizing the risk of retinal tearing, detachment and other damage.

In some embodiments, it may also be desirable to deliver the agent through both the reservoir 2 and the tube 14. In such embodiments, for example, in addition to a tube 14 extending from the distal end 4 of the reservoir 2 or the distal end 12 of the hollow body or tube 10, at least a portion of the reservoir 2 may be fabricated of a material permeable to the agent or the reservoir 2 may have one or more apertures 7 through which the agent may be delivered from the reservoir 2 as discussed above.

The dimensions of the delivery device 1 will depend on the intended application of the device, and will be readily apparent to those having ordinary skill in the art. By way of example, when the delivery device 1 is used to deliver therapeutic agents to the eye, the device is designed for insertion through a small incision, preferably ranging from about 0.25 mm to about 1 mm in diameter, more preferably less than 0.5 mm in diameter, thereby requiring few or no sutures for scleral closure at the conclusion of the procedure. As such, the cross-section of the device 1 with the reservoir 2 compressed preferably ranges from about 0.25 mm to about 1 mm in diameter, and, more preferably, is no greater than 0.5 mm. Preferably, the hollow body or tube 10 has diameter ranging from about 0.5 to about 1.0 mm, and the reservoir 2 may be compressed to the hollow body or tube 10 so as to provide an overall cross section no greater than 1.0 mm. If the hollow body or tube 10 is not tubular, the largest dimension of the cross section can be used to approximate the diameter for this purpose. When used to deliver agents to the posterior chamber of the eye, the device 1 preferably has a length ranging from about 0.5 cm to about 1.5 cm such that when the fixation mechanism 8 is sutured or otherwise secured to the sclera in the region of the pars plana, the delivery mechanism 6 is positioned near the posterior chamber of the eye.

When included in the device 1, the dimensions of the tube 14 will depend on the intended application of the device, and will be readily apparent to those having ordinary skill in the art. By way of example, when used to deliver an agent to the choroids and retinal pigment epithelial cells of the eye, the tube 14 is preferably sized so as to limit delivery rate, to minimize trauma to the retina, and to minimize leaking of agent. As such, the tube 14 preferably has a length ranging from about 1 cm to about 2.5 cm, an outer diameter less than about 0.1 mm, and an inner diameter ranging from about 0.001 mm to about 0.007 mm, and more preferably, from about 0.005 mm to about 0.001.

The use of the delivery device 1 of the present invention can be further understood from the following discussion relating to a method for treating chronic diseases of the eye by sustained release of therapeutic agent to the eye and with reference to FIGS. 1-5.

The delivery device 1 is generally used by the following procedure: the delivery device 1 is prepared with the reservoir 2 empty and preferably compressed, as shown in FIGS. 1a and 4a. If a hollow body or tube 10 is included in the device, the reservoir 2 is preferably compressed about the hollow body or tube 10 as shown in FIG. 1a, to provide a low profile that allows the delivery device 1 to be implanted and removed through a small access incision that requires few or no sutures for closure. If a tube 14 is used for direct delivery of the therapeutic agent to the target site, the first end 16 of the tube 14 is connected to the distal end 4 of the reservoir 2 or the distal end 12 of the hollow body or tube 10.

Figure 5:
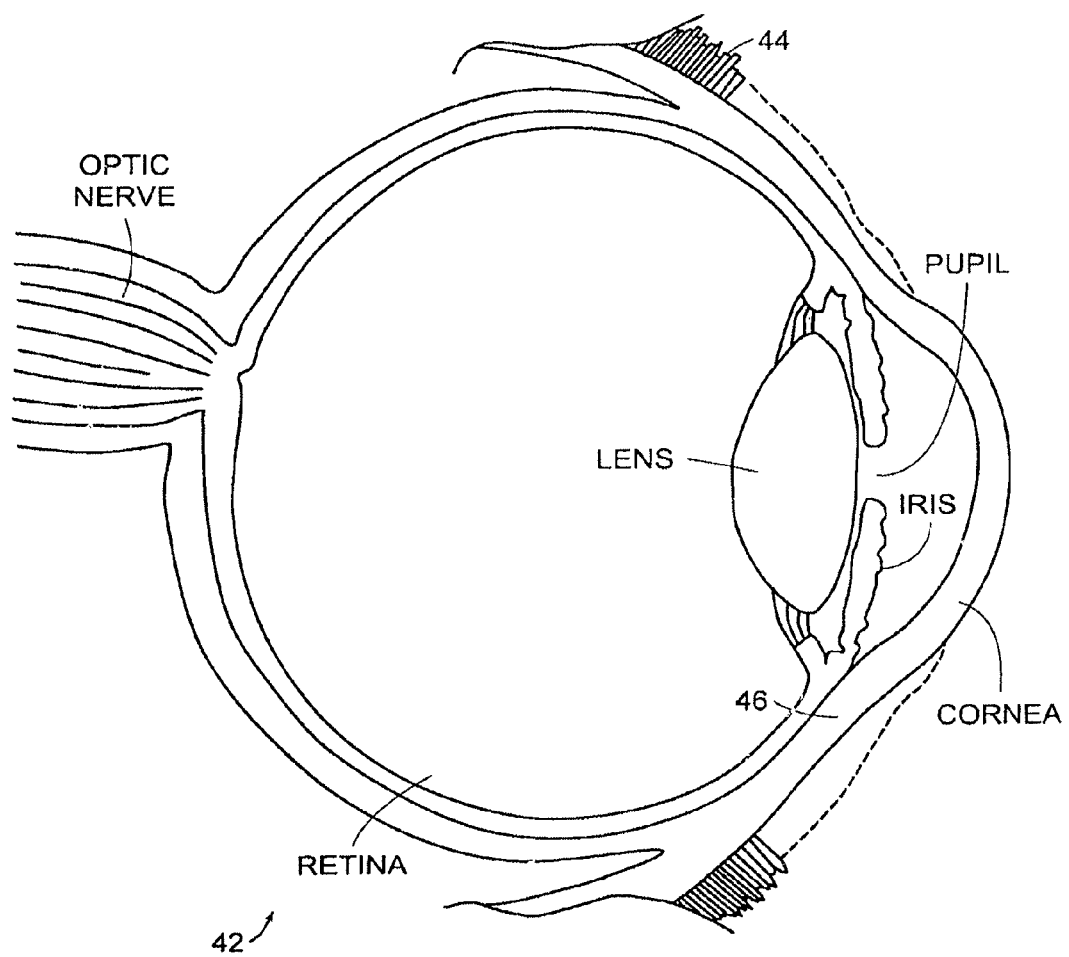
FIG. 5 shows a cross-sectional schematic view of an eye illustrating one 10 technique of pulling back of the conjunctiva to provide access into the eye for insertion of the delivery device of the present invention.

An incision is made to provide access to the treatment site. For example, when used to deliver therapeutic agent to the posterior chamber of the eye, a sclerotomy is created for insertion of the delivery device 1. Conventional techniques may be used for the creation of the sclerotomy. Such techniques require the dissection of the conjunctiva 44 and the creation of pars plana scleral incisions through the sclera 46. As shown in FIG. 5, the dissection of the conjunctiva 44 typically involves pulling back the conjunctiva 44 about the eye 42 so as to expose large areas of the sclera 46 and the clipping or securing of the conjunctiva 44 in that pulled back state (normal position of conjunctiva shown in phantom). In other words, the sclera 46 is not exposed only in the areas where the pars plana scleral incisions are to be made. Surgical instruments used in the procedure are then passed through these incisions. Thus, the incisions created for the procedure must be made large enough to accommodate the instruments required for the procedure.

Alternatively, the creation of the sclerotomy may be accomplished by use of an alignment device and method, such as that described in U.S. Ser. No. 09/523,767 the teachings of which are incorporated herein by reference, that enables sutureless surgical methods and devices therefore. In particular, such methods and devices do not require the use of sutures to seal the openings through which instruments are inserted. The alignment devices are inserted through the conjunctiva and sclera to form one or more entry apertures. Preferably, the alignment devices are metal or polyimide cannulas through which the surgical instruments used in the procedure are inserted into the eye.

The delivery device 1 is then inserted through the incision either by hand or using a variety of insertion devices, e.g. syringe-like devices, known to those of skill in the art. Once safely inside the eye, if the tube 14 is utilized in the application, microforceps or similar positioning mechanisms may be used to position the tube 14 at the treatment location.

The fixation mechanism 8 may then be sutured or otherwise secured to the sclera to hold the delivery device 1 in place. If a cover is used to close the inlet port 5, it is removed at this time, and, if used, a collar for providing a snug fit about the syringe or other injection mechanism is mounted on the inlet port 5. The syringe or other injection mechanism is then connected to the inlet port 5 for injection of the agent into the delivery device 1. If the inlet port 5 is composed of an injectable self-sealing material through which the needle of a syringe or other injection mechanism may be inserted and which seals off automatically when the needle other injection mechanism is removed, the needle or other injection mechanism is simply inserted through the inlet port 5 and the agent injected. Following injection, the conjunctiva may be adjusted to cover the distal end of the device.

When the device is used to deliver ocular agents to the eye for the treatment of a variety of ocular conditions such as, for example, retinal detachment, occlusions, proliferative retinopathy, diabetic retinopathy, inflammations such as uveitis, choroiditis and retinitis, degenerative disease, vascular diseases and various tumors including neoplasms, some agents suitable for delivery to the eye may include, for example, antibiotics such as tetracycline, chlortetracycline, bacitracin, neomycin, polymyxin, gramicidin, cephalexin, oxytetracycline, chloramphenicol, rifampicin, ciprofloxacin, tobramycin, gentamycin, and erythromycin and penicillin; antifungals such as amphotericin B and miconazole; antibacterials such as sulfonamides, sulfadiazine, sulfacetamide, sulfamethizole and sulfisoxazole, nitrofurazone and sodium propionate; antivirals, such as idoxuridine trifluorotymidine, acyclovir, ganciclovir and interferon; antibacterial agents such as nitrofurazone and sodium propionate; antiallergenics such as sodium cromoglycate, antazoline, methapyriline, chlorpheniramine, cetirizine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; decongestants such as phenylephrine, naphazoline, and tetrahydrazoline; miotics and anti-cholinesterase such as pilocarpine, salicylate, carbachol, acetylcholine chloride, physostigmine, eserine, diisopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide; inhibitors of angiogenesis such as angiostatin, anecortave acetate, thrombospondin, and anti-VEGF antibody; and other therapeutic agents such as prostaglandins, antiprostaglandins and prostaglandin precursors.

In some applications, additives may further be included in the agent and, for example, some suitable additives may include water, saline, dextrose, carriers, preservatives, stabilizing agents, wetting agents, emulsifying agents or other similar materials.

In one embodiment, wherein the delivery device 1 comprises a reservoir 2 having an inlet port 5 located near the proximal end 3 of the reservoir 2, the agent injected through the inlet port 5 travels into the reservoir 2. If the reservoir 2 is fabricated of an elastic material, the reservoir 2 inflates/expands as it is filled. When the agent has been injected, the needle or other injection mechanism is removed from the inlet port 5 and the inlet port 5 sealed. The agent in the reservoir 2 is then delivered gradually via the delivery mechanism 6. If tube 14 is included, the agent is delivered through the tube 14 and/or reservoir 2. Once the therapeutic agent had been delivered to the treatment area, the delivery device 1 may be refilled for further delivery or removed if the required dose of agent has been delivered for treatment of the condition. If required, an aspirating device or similar mechanism (not shown) may be used to further compress the reservoir 2, thereby enabling removal of the delivery device 1 through a small incision that requires few or no sutures are required for sclera' closure.

In the embodiment that further comprises a hollow body or tube 10, the agent injected through the inlet port 5 travels through the hollow body or tube 10 and into the reservoir 2 through either the one or more apertures 13 in the hollow body or tube 10 or the distal end 12 of the hollow body or tube. The needle or other injection mechanism is then removed from the inlet port 5 and the inlet port 5 sealed. The agent in the reservoir 2 is then delivered to the treatment area gradually through the reservoir 2 and/or through the distal end 12 of the hollow body or tube 10. If tube 14 is included, the agent is delivered through the tube 14 and/or reservoir 2. Once the therapeutic agent had been delivered to the treatment area, the delivery device 1 may be refilled for further delivery or removed if the required dose of agent has been delivered for treatment of the condition. If required, an aspirating device or similar mechanism (not shown) may be used to further compress the reservoir 2 about the hollow body or tube 10, thereby enabling removal of the delivery device 1 through a small incision that requires few or no sutures are required for scleral closure.

The invention is not be limited to ocular applications, and is particularly useful in other limited access regions such as the inner ear.

The present invention also includes kits that comprise one or more device of the invention, preferably packaged in sterile condition. Kits of the invention also may include, for example, one or more tubes 14, one or more reservoirs 2, means for suturing or securing the fixation mechanism 8 to the sclera, etc. for use with the device, preferably packaged in sterile condition, and/or written instructions for use of the device and other components of the kit.

All documents mentioned herein are incorporated by reference herein in their entirety.

The foregoing description of the invention is merely illustrative thereof, and it is understood that variations and modifications can be effected without departing from the scope or spirit of the invention as set forth in the following claims.

What is claimed is:

1. A sustained release delivery device, the delivery device comprising:
   a refillable reservoir configured to be implanted into a vitreous chamber of an eye through a sutureless sclerotomy and formed a pliable wall configured to contain a therapeutic agent,
   wherein one or more apertures formed in the pliable wall allow for sustained flow of the therapeutic agent contained in the refillable reservoir through the one or more apertures into the vitreous chamber at a rate of delivery, and
   wherein the pliable wall has a first configuration having a first cross-sectional dimension suitable for insertion of the refillable reservoir through the sclerotomy into the vitreous chamber and a second configuration having a second, larger cross-sectional dimension, wherein therapeutic agent flows from the reservoir through the one or more apertures in the pliable wall when in the second configuration so as to deliver the therapeutic agent to the vitreous chamber over an extended period of time at the rate of delivery;
   an inlet port positioned near a proximal end of the refillable reservoir having an injectable, self-sealing surface; and
   an elongated, inner support around which at least a portion of the pliable wall is configured to adopt the first configuration, the inner support comprising a proximal end extending towards the inlet port and a distal end that is external to the pliable wall.

2. The device of claim 1, wherein the one or more apertures formed in the pliable wall are located along a length of the pliable wall of the reservoir.

3. The device of claim 1, wherein the one or more apertures formed in the pliable wall are located at a distal end of the pliable wall of the reservoir.

4. The device of claim 1, wherein a size, a number or a combination of the size and the number of the one or more apertures controls the rate of delivery of the therapeutic agent.

5. The device of claim 1, further comprising a mechanism for controlling the sustained flow of the therapeutic agent through the one or more apertures, wherein the mechanism comprises a porous lining that covers the one or more apertures, a matrix material, a diffusion-limiting material or rate-limiting membrane covering the one or more apertures.

6. The device of claim 1, wherein the pliable wall in the first configuration is folded, rolled or compressed into the first configuration.

7. The device of claim 1, wherein the first cross-sectional dimension is no greater than 0.5 mm in diameter.

8. The device of claim 1, wherein the pliable wall is fabricated of poly(ethylene terephthalate).

9. The device of claim 8, wherein the one or more apertures in the pliable wall are formed with a laser, hot wire, or drilling device.

10. The device of claim 1, wherein the inner support provides additional rigidity for insertion of the reservoir into the vitreous chamber.

11. The device of claim 1, wherein the proximal end of the inner support defines at least a portion of the inlet port.

12. The device of claim 1, further comprising an extension projecting outward from the inlet port, the extension having an upper surface surrounding the injectable, self-sealing surface and a lower surface configured to abut at least an external portion of the sclera surrounding the sclerotomy such that the device is stabilized by the extension.

13. A method for sustained delivery of a therapeutic agent, the method comprising:
   (1) forming a sclerotomy through to a vitreous chamber of an eye, the sclerotomy having a size that requires no sutures for scleral closure;
   (2) preparing an empty sustained release delivery device for implantation in the eye, the sustained release delivery device comprising:
      (i) a refillable reservoir formed of a pliable wall configured to contain the therapeutic agent, wherein one or more apertures are formed in the pliable wall,
      wherein the pliable wall has a first configuration having a first cross-sectional dimension suitable for insertion of the refillable reservoir through the sclerotomy into the vitreous chamber and a second configuration having a second, larger cross-sectional dimension, wherein therapeutic agent flows from the reservoir through the one or more apertures in the pliable wall when in the second configuration so as to deliver the therapeutic agent to the vitreous chamber over an extended period of time at the rate of delivery;
      (ii) an inlet port positioned near a proximal end of the refillable reservoir having an injectable, self-sealing surface; and (iii) an elongated, inner support around which at least a portion of the pliable wall is configured to adopt the first configuration, the inner support comprising a proximal end extending towards the inlet port and a distal end that is external to the pliable wall, wherein preparing comprises compressing the pliable wall of the empty sustained release delivery device into the first configuration;

(3) inserting the compressed, empty reservoir through the sclerotomy into the vitreous chamber until the inlet port remains external to the vitreous chamber;

(4) injecting the therapeutic agent into the reservoir through the inlet port using an injection mechanism;

(5) expanding the compressed reservoir into the second configuration upon injecting the therapeutic agent; and (6) flowing the therapeutic agent from the reservoir through the one or more apertures formed in the pliable wall into the vitreous chamber so as to deliver the therapeutic agent at a desired rate of delivery.

14. The method of claim 13, further comprising controlling the rate of delivery of the therapeutic agent by altering a size, a number or a combination of the size and the number of the one or more apertures.

15. The method of claim 13, further comprising controlling the rate of delivery of the therapeutic agent through the one or more apertures with a porous lining that covers the one or more apertures, a matrix material, a diffusion-limiting material or rate-limiting membrane covering the one or more apertures.

16. The method of claim 13, wherein compressing the pliable wall of the empty sustained release delivery device into the first configuration further comprises folding or rolling the pliable wall into the first configuration.

17. The method of claim 13, wherein the first cross-sectional dimension is no greater than 0.5 mm in diameter.

18. The method of claim 13, wherein the pliable wall is fabricated of poly(ethylene terephthalate).

19. The method of claim 18, wherein the one or more apertures are formed with a laser, hot wire, or drilling device.

20. The method of claim 13, further comprising filling the reservoir inserted within the vitreous chamber with an additional amount of the therapeutic agent using an injection mechanism inserted through the inlet port positioned external to the vitreous chamber.

21. The method of claim 13, further comprising compressing the reservoir back to the first configuration after the therapeutic agent is delivered and removing the device from the sclerotomy, wherein removing the device requires no sutures for scleral closure.

* * * * *